United States Patent [19]

Harwin

[11] Patent Number: 6,013,077
[45] Date of Patent: Jan. 11, 2000

[54] ORTHOPAEDIC POSTING DEVICE

[76] Inventor: Steven F. Harwin, 1050 Park Ave., New York, N.Y. 10028

[21] Appl. No.: 08/904,048
[22] Filed: Jul. 31, 1997
[51] Int. Cl.[7] ..................................................... A61B 17/56
[52] U.S. Cl. ............................... 606/72; 606/73; 606/75; 606/232
[58] Field of Search ................................ 606/75, 72, 73, 606/104, 232

[56] References Cited

U.S. PATENT DOCUMENTS

| | | | |
|---|---|---|---|
| 4,988,351 | 1/1991 | Paulos et al. | 606/72 |
| 5,013,316 | 5/1991 | Goble et al. | 606/72 |
| 5,662,655 | 9/1997 | Laboureau et al. | 606/75 |
| 5,725,541 | 3/1998 | Anspach, III et al. | 606/151 |

*Primary Examiner*—Michael Buiz
*Assistant Examiner*—Julian W. Woo
*Attorney, Agent, or Firm*—Graham & James LLP

[57] ABSTRACT

A drive-in posting device for use in tightly holding sutures in place such as for orthopaedic procedure involving bone grafting. The posting device comprises a nail-like tine made of a biologically acceptable material such as stainless steel, vitalium, titanium and the like, as well as hard bioabsorbable materials. Alternatively the posting device comprises a screw shank and is inserted by being screwed into the bone. The posting device is provided with a head having an integral washer and three or four lateral extension elements or an extension clover leaf on which suture wire can be wrapped and tightened. The tine is optionally provided with an eye through which the suture is threaded. The head of the posting device is configured for use with a rotational driver and the extension elements are provided with short tines which face and are engageable with a bone. In operation, the body tine is partially driven into a bone and a suture is threaded through the eye or otherwise wrapped therearound. The posting device is then rotated by means of a driver inserted into an engagement member of the head of the device. The suture is thereby tightened as required in a manner similar to the tightening of violin strings. When a requisite tension is obtained, the posting device is driven into the bone, with the short tines being driven into the bone to prevent rotational loss of tension. To prevent accidental removal, the tines may be provided with one way barbs.

12 Claims, 2 Drawing Sheets

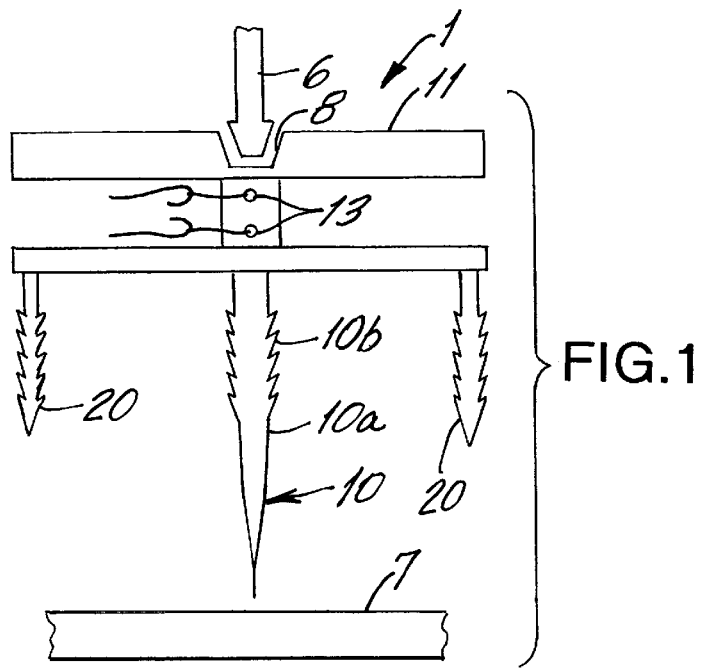
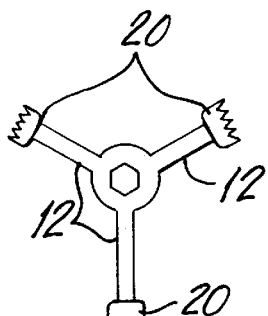
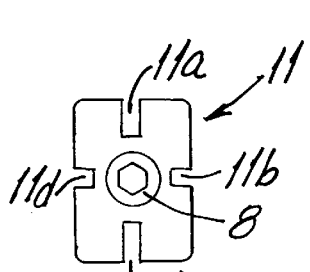
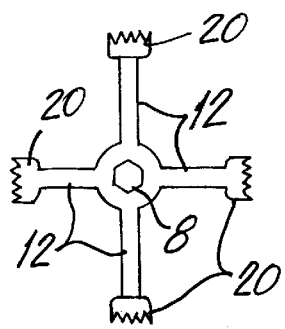
FIG.3a  FIG.2  FIG.3b
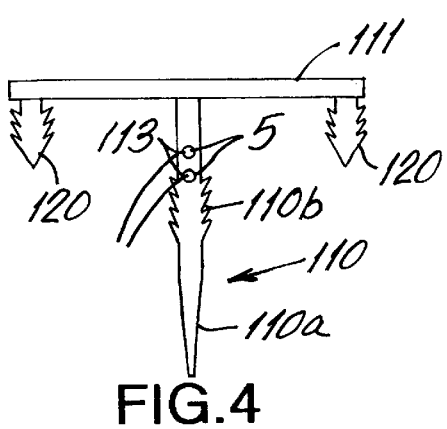
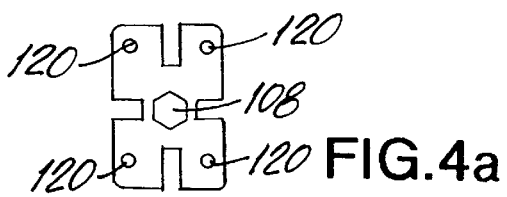
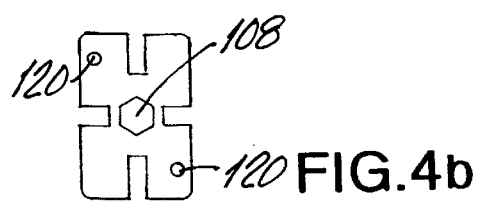
FIG.4  FIG.4a  FIG.4b

ORTHOPAEDIC POSTING DEVICE

FIELD OF THE INVENTION

This invention relates to posting devices for the fixed holding of sutures and in particular to posting devices which are driven into bones during orthopaedic procedures for the fixed holding of sutures.

BACKGROUND OF THE INVENTION

Posting devices, as they are referred to, are utilized in orthopaedic surgery as devices on which sutures are tightened for the fixed tensioning and holding of such sutures, as may be required in various orthopaedic procedures such as with bone grafts. The posting devices are generally configured in the form of nails or screws, with head elements similar to those of standard screws and nails, and the posting devices are used with separate washer elements.

In use, the nail-configured posting devices are driven into a bone by impacting, such as with a driver. Posting devices, in the form of a screw, are rotatably inserted with a screw driver. In each embodiment the posting device is not initially completely seated so that suture can be engaged with or wrapped around under the head of the device and tensioned such as by pulling on the suture until a desired tension is reached. The suture is then fixed onto the posting device, against loosening, by the continued driving or screwing of the device into the bone until the wrapped suture is compressingly held between the nail or screw head and the washer used therewith.

There are several problems inherent with such posting devices, foremost of which is the difficulty of wrapping or tightening a suture against a screw or nail with only a minimal portion thereof extending over a bone surface for engagement with the suture material. An additional problem is that of gradual loosening of the tensioned posting device and suture, over extended periods of time, particularly with respect to the nail-like drive-in device with minimal frictional contact between bone and smooth nail shank surface.

SUMMARY OF THE INVENTION

It is an object of the present invention to provide a posting device which provides for an enhanced area for facilitated suture engagement and fixing.

It is a further object of the present invention to provide a posting device with enhanced resistance against both pull out and loosening over time. Generally the present invention comprises a suture posting device comprising a drive-in tine member which can be partially imbedded in bone to a desired initial depth. For facility in fastening and fixing a suture in position, the posting device of the present invention further comprises a head with lateral extension members upon which the suture can be wound, interleaved and fastened. The extension members further comprise position fixing means such as small tines, which, when driven into the bone, to complete the suture fixing, prevent reversing rotational movement and loosening of the suture. It is understood that the position fixing means need not be present on each extension member and that a single one can be sufficient for the requisite purpose of preventing suture loosening, though it is preferred that the tines be symmetrical in placement, to avoid skewed drive-in.

In a second embodiment of the present invention, the posting device comprises a screw in member with an integral washer head having a laterally extending head which frictionally engages and clamps the suture and the bone to prevent loosening, in conjunction with the increased surface area between screw threads and bone.

In both embodiments, the posting device further comprises means, integral with the head thereof, for the clamped engagement with a tightened suture, for maintaining suture tension. The head further comprises means for engagement with a rotating driver such as a screw driver, hex driver (allen wrench), nut driver, etc., for initially effecting the requisite tightening and tension.

The above objects, features and advantages of the present invention will become more evident from the following discussion and drawings in which:

SHORT DESCRIPTION OF THE DRAWINGS

FIG. 1 is a side view of a first embodiment of the posting device of the present invention;

FIGS. 2 is a top view of the head of the posting device of FIG. 1;

Figure 5:
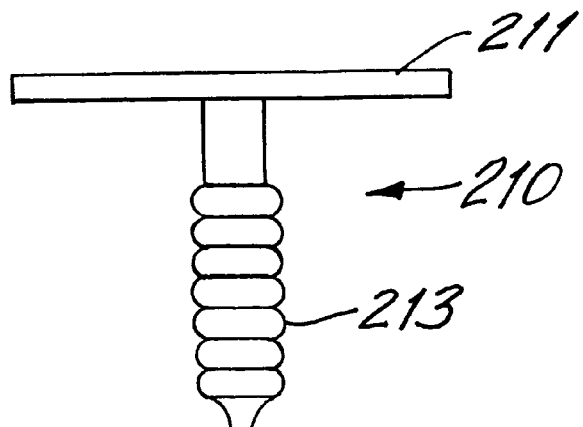
Figure 5A:
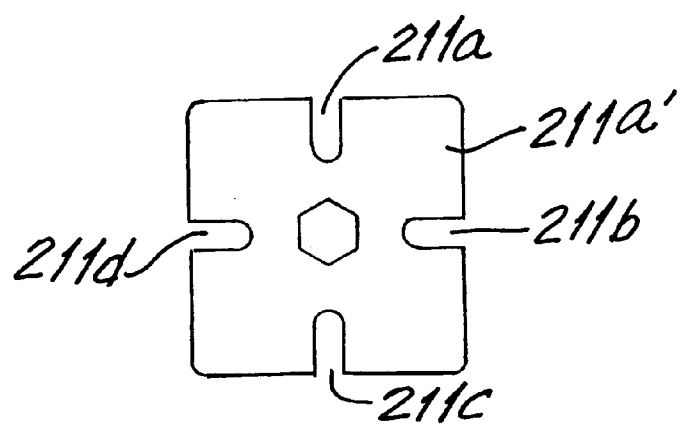
Figure 5B:
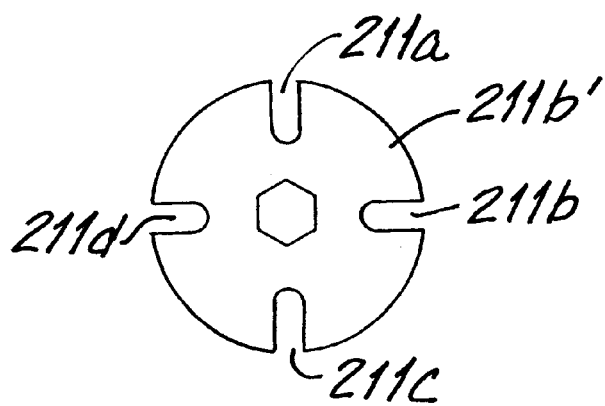

FIGS. 3a–b depict two top view alternative configurations of barbed tines and extensions possible with the posting device of FIG. 1;

FIG. 4 is a side view of a second embodiment of the posting device of the present invention, with the extensions and tines being integrated in a unitary head;

FIGS. 4a and 4b are alternative views of heads for the embodiment of FIG. 4;

FIG. 5 is a side view of a third embodiment of the posting device of the present invention with a screw insertion and integral wrapping washer head; and FIGS. 5a and 5b are alternative views of heads for the embodiment of FIG. 5.

DETAILED DESCRIPTION OF THE INVENTION

Generally the present invention comprises a drive-in posting device for use in tightly holding sutures in place such as for orthopaedic procedure involving bone grafting. The posting device comprises a nail-like tine (and in another embodiment a screw like shank) made of a biologically acceptable material such as stainless steel, vitalium, titanium and the like, as well as hard bioabsorbable materials. The posting device is provided with a head having an integral washer and three or four lateral extension elements or an extension clover leaf on which suture wire can be wrapped and tightened. The tine is optionally provided with an eye through which the suture is threaded. The head of the posting device is configured for use with a rotational driver and the extension elements are provided with short tines which face and are engageable with a bone. In operation, the body tine is partially driven into a bone and a suture is threaded through the eye or otherwise wrapped therearound. The posting device is then rotated by means of a driver inserted into an engagement member of the head of the device. The suture is thereby tightened as required in a manner similar to the tightening of violin strings. When a requisite tension is obtained, the posting device is driven into the bone, with the short tines being driven into the bone to prevent rotational loss of tension. To prevent accidental removal, the tines may be provided with one way barbs.

In a preferred embodiment of the present invention the central tine of the posting device comprises one or more eyelets for the insertion of suture therethrough for the snugging up of the suture and the fixed tieing thereof. The lateral extension members may extend either directly from the head of the central tine itself or the lateral extension members may extend from the shaft of the tine, a distance below the head. In such latter embodiment a slight protrusion of the posting device remains above the level of the bone. In both embodiments, the shaft wall of the central tine is round and smooth at its lower extremity in initially engagement with the bone. The remaining surface of the upper portion of tine shaft may optionally have short fixation barbs to resist unwanted withdrawal forces.

In operation, the posting device is initially impact inserted into the bone for a distance corresponding to the smooth surface of the central tine. The suture is tied through eyelets in the central tine or is wrapped or interleaved around the extension members (the bore hole is accordingly sized to allow room for the suture). Thereafter the posting device is forcibly rotated by a tool, such as screw drive, hex driver and the like (depending on the co-fitting driver-engagement configuration of the head of the posting device). The smooth lower surface of the tine readily permits such rotation without excessive trauma to the bone. Thereafter, when the desired suture tension is obtained, the posting device is driven into the bone with the barbed portion engaging the walls of the aperture formed by the initial insertion of the tine. With the driving of the central tine into the bone, smaller tines (preferably barbed as well) extending down off the ends of the extension members are also driven into the bone, with such latter tines further preventing unwanted withdrawal as well as reverse rotation and loosening of the suture ties. Not all the extension elements need have the small "anti-rotation" tines but they should be placed symmetrically to avoid tilting and skewed driving of the posting device into the bone.

With the embodiment having a screw shank it is not practicable to have drive-in tines to prevent reverse rotation. Instead, frictional engagement is enhanced by means of an integrated washer head which is used to wrap the suture therearound and to clamp the suture against the bone. The increased frictional engagement combined with the screw thread frictional engagement serves to substantially prevent loosening. However, it is preferred that the suture clamping surface of the integral washer be smooth in order to avoid cutting of the washer with tightening of the screw threaded posting device.

DETAILED DESCRIPTION OF THE DRAWINGS AND THE PREFERRED EMBODIMENTS

With reference to the drawings, in FIG. 1, posting device 1 is shown with central tine 10 having a smooth, rounded portion 10a and barbed portion 10b. The head 11 of the posting device is outwardly laterally extending to facilitate tying of suture thereon or therearound. The head 11 of the posting device is a clover leaf configuration as more clearly seen in FIG. 2, with notches 11a–d, available for suture fitment and tying. In addition, central tine 10 is configured with eyelets 13 for insertion of suture therethrough (threading through two or more of the eyelets and tying of the end provides an effective posting). Lateral extensions 12 (three shown in FIG. 3a and four in FIG. 3b) are provided with short barbed tines 20 with insertion tips being at or slightly above the level of smooth section 10a of central tine 10.

In operative use, the posting device 1 is positioned on a bone 7 requiring use thereof, and impacted into the bone 7 such that only smooth section 10a is imbedded in the bone and wherein tines have not been engaged with the bone. Suture 5, is threaded through eyelets 13, snugged, and tied. A driving tool such as a hex socket 6 is fitted into a corresponding drive engaging element 8 in head 11, and the posting device is rotated (the smooth shaft portion 10a of central tine 10 permits such rotation) until the suture is properly tensioned. The driving tool 6 is removed and the head of the posting device is impacted (the driving tool itself can be configured to be used for the impacting) to cause the tines 20 and the barbed section 10b of central tine 10 to penetrate the bone. Loosening of the suture, because of gradual relaxing of the engagement between a tine and bone, under continued tension pressure, is prevented by the peripheral anti-rotation tines.

In the alternative embodiment shown in FIG. 4, a cloverleaf head 111 embodies the anti-rotation tines 120 depending directly from the periphery thereof. Central tine 110, similarly has smooth section 110a and barbed section 100b, with the former being initially imbedded in the bone. Suture 5 is threaded through eyelets 113 and tied, as with the first embodiment. Rotation for tensioning is effected by means of a hex head driver engaged with the hex head 108 shown in FIGS. 4a and 4b, with smooth section 110a permitting the rotation. After proper tensioning, as before, the head 111 is impacted to cause the barbed section 110b of central tine 110 and barbed anti-rotation tines 120 (two shown symmetrically diagonally disposed in FIG. 4b and four tines fully disposed as shown in FIG. 4a) to penetrate the bone. In this embodiment, the suture itself is imbedded into the bone together with the posting device.

In the embodiment shown in FIGS. 5, 5a and 5b, screw threaded posting device 210 is provided with integral laterally extending washer head 211, with the alternative washer head configurations 211a and 211b, shown in FIGS. 5a and 5b (square and round clover-leaf), which extending washer heads effect a clamping against suture wire and bone into which it is installed by a screwing insertion. Cutouts 211a–d in each of the head embodiments may be used for securely tying suture thereon. Screw threads 213 prevent pull-out from a bone and provide a partial frictional resistance to loosening.

It is understood that the above discussion and drawings of preferred embodiments is merely exemplary of the present invention and that changes may be made in structure, configuration and relative placement of elements of the posting device without departing from the scope of the present invention as defined in the following claims.

What is claimed is:

1. A posting device for posting sutures in bones, wherein the posting device comprises a central tine for impact driving into a bone; means for affixing suture to the posting device; a head comprising a recessed portion and configured for use with a driver for the rotation of the central tine in the bone, whereby the affixed suture is tightened to a desired tension; and wherein the posting device further comprises at least one element extending lateral to the central tine, having imbedding means thereon, for imbedding in the bone only after the affixed suture is tightened, and for preventing rotation of the central tine and loosening of the suture.

2. The posting device of claim 1, wherein the central tine comprises a smooth segment which is adapted to be initially driven into the bone and rotated therein, and a one-way barbed segment adapted to be driven into the bone after the suture is tightened.

3. The posting device of claim 2, wherein the imbedding means comprises at least one tine, which is shorter than the central tine, and which is positioned above the smooth segment of the central tine, relative to the bone.

4. The posting device of claim 2, wherein the central tine comprises at least one eyelet extending through a thickness thereof for the insertion therethrough of the suture.

5. The posting device of claim 2, wherein the laterally extending element extends laterally from the head.

6. The posting device of claim 2, wherein the laterally extending element extends laterally from the central tine and is spaced from the head.

7. The posting device of claim 5, wherein the laterally extending element comprises a clover leaf configuration and wherein the imbedding means comprises at least two tines, each of which is shorter than the central tine, and each of which is positioned above the smooth segment of the central tine, relative to the bone with the short tines depending from diagonal leafs of the clover leaf configuration.

8. The posting device of claim 5, wherein the posting device comprises three symmetrically disposed extending arms, and wherein the imbedding means comprises three tines, each of which is shorter than the central tine, and each of which is positioned above the smooth segment of the central tine, relative to the bone, with the three short tines depending from the three extending arms respectively.

9. The posting device of claim 5, wherein the device comprises four symmetrically disposed extending arms, and wherein the imbedding means comprises four tines, each of which is shorter than the central tine, and each of which is positioned above the smooth segment of the central tine, relative to the bone, with the four short tines depending from the four extending arms respectively.

10. The posting device of claim 6, wherein the laterally extending element comprises a clover leaf configuration and wherein the imbedding means comprises at least two tines, each of which is shorter than the central tine, and each of which is positioned above the smooth segment of the central tine, relative to the bone with the short tines depending from diagonal leafs of the clover leaf configuration.

11. The posting device of claim 6, wherein the posting device comprises three symmetrically disposed extending arms, and wherein the imbedding means comprises three tines, each of which is shorter than the central tine, and each of which is positioned above the smooth segment of the central tine, relative to the bone, with the three short tines depending from the three extending arms respectively.

12. The posting device of claim 6, wherein the posting device comprises four symmetrically disposed extending arms, and wherein the imbedding means comprises four tines, each of which is shorter than the central tine, and each of which is positioned above the smooth segment of the central tine, relative to the bone, with the four short tines depending from the four extending arms respectively.

* * * * *